United States Patent [19]
Kaufman

[11] Patent Number: 6,014,973
[45] Date of Patent: Jan. 18, 2000

[54] METHOD AND DEVICE FOR HEALING

[76] Inventor: Lauren Kaufman, 1228 Montgomery No. 6, San Francisco, Calif. 94133

[21] Appl. No.: 09/002,015

[22] Filed: Dec. 31, 1997

[51] Int. Cl.⁷ ..................................................... A61B 19/00
[52] U.S. Cl. ........................................... 128/897; 128/898
[58] Field of Search .................................... 128/898, 897; 600/9, 15, 26

[56] References Cited

U.S. PATENT DOCUMENTS 5,147,294  9/1992  Smith et al. ............................. 128/898

*Primary Examiner*—Linda C. M. Dvorak
*Assistant Examiner*—Rosiland Kearney
*Attorney, Agent, or Firm*—Finley & Berg, LLP

[57] ABSTRACT

A method of healing a living body and a device are provided comprising a combination of five healing elements: a first healing element comprising moss agate, a second healing element comprising copper, a third healing element comprising malachite, a fourth healing element comprising tourmaline, and a fifth healing element comprising a skeletal material from a once-living creature. The method comprises the steps of supporting each of the healing elements in a position proximate to or in direct contact with a living body, either simultaneously or in sequence. The device for effecting this healing method comprises a securing means to which the above described healing elements are secured.

25 Claims, No Drawings

METHOD AND DEVICE FOR HEALING

FIELD OF THE INVENTION

This invention relates to devices and methods for healing a living body through application of healing elements to or near the body.

BACKGROUND OF THE INVENTION

Many well known non-invasive healing methods operate by application of various items to the body of a person or animal. Pressure-oriented methods of healing include acupressure, which is used to stop pain and cure disease by applying pressure to key nerve centers about the body; massage techniques, which offer pain relief and muscle relaxation; and chiropractic medicine, which can even realign misaligned body parts. These techniques generally require training and practice to master, and are best utilized when a skilled practitioner applies the techniques to a patient, requiring expensive and time consuming personal attention.

In herbal medicine (phytopharmacognosy), treatments are often carried out through contact between the person to be healed and various plant materials. While some of these therapies involve breathing in odors or fumes produced from the herbs used, many simply require application of the herbs to the skin, in the form of lotions, poultices, tinctures, liniments, and the like. These treatments are known to provide pain relief, remedy skin irritations, relax tense muscles, and more. However, because herbal therapies rely on plant materials which eventually degenerate, they require that new materials be purchased periodically if the therapeutic technique is to be reapplied. Additionally, the herbs used in these therapies can create odors or skin sensations which are undesirable in some instances.

Other therapies have been developed which utilize natural materials including crystals, metals, and gemstones applied to the body to provide distinct healing effects. These therapies, conventionally known as "crystal therapies," are desirable because they use durable materials which can be used repetitively with no loss of function, produce no known detrimental side effects, and do not require professional supervision or application.

However, conventional crystal therapies focus on the known effects generated by a particular material when used individually. Crystal therapy healers have used a mix and match approach in which they simply select materials, as needed, known for having particular healing effects. This approach fails to consider or recognize that the use of a combination of materials is often accompanied by synergistic healing properties.

A primary object of the present invention is to provide a combination of materials, previously not utilized by conventional healing techniques, that safely and reliably heals bodily ailments including, but not limited to, aches and pains, inflammation, sprains, arthritis, muscle stiffness, carpal tunnel, and injuries.

Another object of the present invention is to heal a living body using a non-invasive method.

A further object of the present invention is to heal a living body by applying re-usable, durable, and affordable components.

Other objects and advantages of the present invention will become apparent when the method and device of the present invention is considered in conjunction with the accompanying specification and claims.

SUMMARY OF THE INVENTION

The present invention overcomes the shortcomings of conventional techniques by providing a method of healing a living body and a device which comprises a novel combination of healing elements: a first healing element comprising moss agate, a second healing element comprising copper, a third healing element comprising malachite, a fourth healing element comprising tourmaline, and a fifth healing element comprising a skeletal material from a once-living creature. The method comprises the steps of supporting each of the healing elements in a position proximate to or in direct contact with a living body, either simultaneously or in sequence. The device for effecting this healing method comprises a securing means to which the above described healing elements are secured.

DESCRIPTION OF THE PREFERRED EMBODIMENT

The inventive method operates by applying the healing properties of five key materials to establish substantial healing effects in a living body. These five materials, referred to herein as "healing elements," are: (1) moss agate, (2) copper, (3) malachite, (4) tourmaline, and (5) skeletal material from a once-living creature. These healing elements are widely available from conventional suppliers.

While the present invention is preferably applied to the human body, it should be understood that the inventive method and device may also be applied to the body of an animal.

The inventive method comprises the following steps: supporting the first healing element, comprising moss agate, in a first position proximate to or in direct contact with the body; supporting a second healing element, comprising copper, in a second position proximate to or in direct contact with the body; supporting a third healing element, comprising malachite, in a third position proximate to or in direct contact with the body; supporting a fourth healing element, comprising tourmaline, in a fourth position proximate to or in direct contact with the body; and supporting a fifth healing element, comprising a skeletal material from a once-living creature, in a fifth position proximate to or in direct contact with the body. Preferably, these steps are all taken simultaneously; however, the healing method will still operate even where there is some delay between supporting each healing element proximate to the body. Where the steps are performed sequentially rather than simultaneously, they may be followed in any order.

Preferably, the elements described are placed in direct contact with the body. It is also suitable for the elements to be "proximate to" the body without contact occurring. The healing elements should be considered to be proximate to the body if they are located within a three foot range from the body.

The healing elements may be used in their roughly natural states (as a rock or pellet, ore, a bone fragment, etc.). Preferably, the tourmaline of the fourth healing element is black. A preferred skeletal material for the fifth healing element is bone, but other skeletal materials such as shell or antler may also be utilized. None of the healing elements is required to have a particular form. The healing elements may be shaped as desired into beads or other designs. Beads, whether spherical, prismatic, or otherwise, are a preferred form for the healing elements as they may be easily secured to securing means such as a bracelet, necklace, anklet or the like.

The preferred device utilizes a securing means upon which each of the above five healing elements is secured. A preferred securing device is a flexible strand suitable for wear upon the body. The strand may then be worn as a necklace, bracelet, anklet, etc., or may be wrapped around a particular site of pain or injury, such as a sprain or cut. A preferred means of securing the healing to such a flexible strand is to form each healing element into the shape of a bead defining a hole therethrough. Each hole should be of sufficient size to allow the flexible strand to pass through it. By passing the flexible strand through the hole of each bead, the beads are secured to the flexible strand.

Alternative methods of supporting the healing elements proximate to or in direct contact with the body include, but are not limited to, placing them within a pouch worn on the body, or grinding the healing elements into the form of a paste, powder, lotion, or cream rubbed on to the body.

Noticeable healing will occur even where small quantities of each healing element are used, on the order of a mass of one gram. Similarly, as long as all five types of healing elements are present, no specific proportions between the elements are required. A preferred device uses healing elements in a way such that the collective mass of equal amounts of the first and third healing elements (moss agate and malachite) is approximately equal to two thirds of the collective mass of equal amounts of the second, fourth, and fifth healing elements (copper, tourmaline, and the skeletal material). An alternative embodiment employs approximately equal masses of all five healing elements.

In the preferred embodiment of the method, and the preferred use of the healing device, the positions in which the healing elements and/or device are placed are contact points on the body proximate to a desired healing site, which typically will be a site of pain, inflammation, skin irritation, or injury. However, healing effects will be produced by supporting the elements anywhere proximate to the body. An alternative is to place individual healing elements in direct contact with chakra points about the body. Chakra points include, but are not limited to, the crown at the top of the head, associated with the pineal gland; the brow, associated with the pituitary gland; the throat, associated with the thyroid and parathyroid glands, the heart, associated with the heart and thymus glands, and the solar plexus, associated with the pancreas and adrenal glands.

The inventive method and device have consistently produced substantial healing for a variety of injuries and ailments. The inventive method and device have successfully been used to treat conditions including, but not limited to, aches and pains, muscle stiffness, sprains, inflammation, arthritis, carpal tunnel, and sports injuries. They have also been used to improve the overall health, vitality, and energy of their user.

An alternative embodiment of the inventive method and device utilizes a sixth healing element comprising blue lace agate. It has been found that the addition of this sixth healing element amplifies the healing effects of the first five healing elements when treating particularly severe ailments. This embodiment has also proven particularly effective in the treatment of bone disorders including, but not limited to, osteo arthritis. In the method, the sixth healing element is supported in a sixth position proximate to or in direct contact with the body, again either simultaneously or sequentially with the support of the first five healing elements. In the device, the sixth healing element is secured upon the securing means.

As is often the case in other therapies, such as herbal therapy, it is not understood for each of these materials every characteristic of the material that causes the healing to occur. Primary characteristics of the healing elements known to cause effects in the body include their electromagnetic and thermal properties. Each material, as well as the body, innately stores a certain amount of electromagnetic energy, and has a discrete conductivity. Wearing the healing elements proximate to or in direct contact with the body can both provide an exchange of electrical energies between each element and the body, as well as affect the body's conduction of its own electrical system. Similarly, when supported on or near the body, temperature differences between the healing elements and the skin cause heat exchanges to occur. As each of the healing elements and the body have different thermal characteristics, each supplies a different heat exchange rate.

Healing effects have been consistently produced where the healing elements are placed near to the body rather than on the body. However, applications of the healing method and device wherein the healing elements are placed on the body are preferred, as additional healing effects of the inventive method and device may derive from the weight exerted by the healing elements on the body by gravity and as contact between the healing elements and the skin accentuates the ease and rapidity with which energy can be transferred between the healing elements and the body.

The materials used for the healing elements are durable and will not appreciably wear down through use. However, the energy stored in the healing elements, including but not limited to thermal and electromagnetic energy, will require replenishing. The healing elements can be thus replenished by "cleansing" them; cleansing can be accomplished by placing the healing elements in extremes of hot or cold via sunlight or a freezer. Additionally, the healing elements work most effectively when they are periodically washed; preferably, they are washed using sea salts.

The amount of time for which the healing elements should be supported proximate to or in direct contact with the body in order to cause substantial healing to occur will vary by the individual case. It is preferred that the healing elements be simultaneously maintained in position for at least ten minutes at a time. No undesirable side effects have been reported where the inventive method or device have been used for extended periods of time. However, as the healing elements periodically require cleansing, prolonged use of the healing elements without cleansing will gradually produce fewer effects. It should also be noted that as smaller quantities of the healing elements are used, cleansing of the healing elements will be required more frequently, as the energy stored in small healing elements is more quickly depleted than in larger healing elements.

Although the foregoing invention has been described in some detail by way of illustration for purposes of clarity of understanding, it will be readily apparent to those of ordinary skill in the art in light of the teachings of this invention that certain changes and modifications may be made thereto without departing from the spirit or scope of the appended claims.

It is claimed:

1. A method of healing a living body, comprising:
   supporting a first healing element comprising moss agate in a first position proximate to said body;
   supporting a second healing element comprising copper in a second position proximate to said body;
   supporting a third healing element comprising malachite in a third position proximate to said body;
   supporting a fourth healing element comprising tourmaline in a fourth position proximate to said body;

supporting a fifth healing element comprising a skeletal material from a once-living creature in a fifth position proximate to said body.

2. The method of claim 1, wherein all of said healing elements are approximately equal in mass.

3. The method of claim 1, wherein the collective mass of said first element and said third element is equal to two-thirds of the collective mass of said second element, said fourth element, and said fifth element.

4. The method of claim 3, wherein said first element and said third element have equal masses and said second element, said fourth element, and said fifth element have equal masses.

5. The method of claim 2, wherein said skeletal material of said fifth healing element is bone.

6. The method of claim 2, wherein said skeletal material of said fifth healing element is shell.

7. The method of claim 2, wherein said skeletal material of said fifth healing element is antler.

8. The method of claim 5, further comprising the step of maintaining said healing elements simultaneously in said supported positions for at least ten minutes.

9. The method of claim 8, wherein said healing elements are secured upon a flexible strand suitable for wear upon said body, said strand supporting said healing elements in said first, second, third, fourth, and fifth positions, respectively.

10. The method of claim 9, wherein said healing elements are each shaped in the form of a bead, each bead defining a hole therethrough, and wherein said flexible strand is passed through said holes in said beads to secure said beads.

11. The method of claim 8, wherein said healing elements are held within a pouch, said pouch supporting said healing elements in said first, second, third, fourth, and fifth positions, respectively.

12. The method of claim 5, further comprising the step of supporting a sixth healing element comprising blue lace agate in a sixth position proximate to said body.

13. A method of healing a living body, comprising:
supporting a first healing element comprising moss agate in a first position in direct contact with said body;
supporting a second healing element comprising copper in a second position in direct contact with said body;
supporting a third healing element comprising malachite in a third position in direct contact with said body;
supporting a fourth healing element comprising tourmaline in a fourth position in direct contact with said body;
supporting a fifth healing element comprising a skeletal material from a once-living creature in a fifth position in direct contact with said body.

14. The method of claim 13, wherein said first, second, third, fourth, and fifth positions are contact points on said body proximate to a healing site on said body.

15. The method of claim 13, wherein said first, second, third, fourth, and fifth positions are chakra points on said body.

16. The method of claim 13, further comprising the step of supporting a sixth healing element comprising blue lace agate in a sixth position in direct contact with said body.

17. A device for healing a living body, comprising:
a securing means for securing healing elements;
a first healing element comprising moss agate secured to said securing means;
a second healing element comprising copper secured to said securing means;
a third healing element comprising malachite secured to said securing means;
a fourth healing element comprising tourmaline secured to said securing means;
a fifth healing element comprising a skeletal material from a once-living creature secured to said securing means.

18. The device of claim 17, wherein all of said healing elements are approximately equal in mass.

19. The device of claim 17, wherein the collective mass of said first element and said third element is equal to two-thirds of the collective mass of said second element, said fourth element, and said fifth element.

20. The device of claim 19, wherein said first element and said third element have equal masses and said second element, said fourth element, and said fifth element have equal masses.

21. The device of claim 18, wherein said skeletal material of said fifth healing element is bone.

22. The device of claim 18, wherein said skeletal material of said fifth healing element is shell.

23. The device of claim 18, wherein said skeletal material of said fifth healing element is antler.

24. The device of claim 21, wherein said securing means is a flexible strand suitable for wear upon said body.

25. The device of claim 24, wherein said healing elements are each shaped in the form of a bead, each bead defining a hole therethrough, and wherein said flexible strand is passed through said holes in said beads to secure said beads.

* * * * *